(12) United States Patent
Yoon et al.

(10) Patent No.: US 6,531,633 B2
(45) Date of Patent: Mar. 11, 2003

(54) TRIARYLPHOSPHINE OXIDE DERIVATIVES CONTAINING FLUORINE SUBSTITUENT AND PREPARING METHOD THEREOF

(75) Inventors: Tae-Ho Yoon, Kwangju (KR); Kwang Un Jeong, Kwangju (KR); Young-Jun Jo, Kwangju (KR)

(73) Assignee: Kwangju Institute of Science and Technology, Kwangju (KR)

( * ) Notice: Subject to any disclaimer, the term of this patent is extended or adjusted under 35 U.S.C. 154(b) by 0 days.

(21) Appl. No.: 09/884,964

(22) Filed: Jun. 21, 2001

(65) Prior Publication Data

US 2002/0095057 A1 Jul. 18, 2002

(30) Foreign Application Priority Data

Jan. 15, 2001 (KR) .......................................... 2001-2263

(51) Int. Cl.⁷ .................................................. C07F 9/53
(52) U.S. Cl. ........................................................ 568/14
(58) Field of Search .............................. 568/14, 15, 16, 568/17

(56) References Cited

U.S. PATENT DOCUMENTS 6,342,638 B1 * 1/2002 Yoon et al. .................... 568/14

OTHER PUBLICATIONS

CA:123:112190 abs of J Org Chem By Whitaker et al 60(11) pp 3499–508 1995.*
CA:133:207946 abs of Organic Letters by Chen et al 2(17) pp 2675–2677 Aug. 2000.*
CA:134:147655 abs of Journal of Organic Chem by Zhang et al 65(26) pp 8866–8873 2000.*
Tetrahedron Letters by Chen et al "Novel and efficient synthesis of perfluoroalkylated arylphosphines" vol. 41 pp 3697–3700 Mar. 2000.*
K. Jeong et al., Synthesis and Characterization of Novel Aromatic Polyimides from Bis (3–aminophenyl) 3,5–bis(trifluoromethly) peenyl Phosphine Oxide, Korea Polymer Journal, vol. 8, No. 5, pp. 215–223 (2000).
M.F. Martinez–Núñez, et al.; Synthesis and Characterization of Polyimides Using a Novel Phosphorus Containing Diamine, Polymer Reprint, vol. 35, p. 709 (1994).

* cited by examiner

Primary Examiner—Jean F. Vollano
(74) Attorney, Agent, or Firm—Finnegan, Henderson, Farabow, Garrett & Dunner, L.L.P.

(57) ABSTRACT

The present invention relates to fluorine-containing triarylphosphine oxide derivatives and preparing method thereof. Particularly, the present invention relates to both fluorine- and phosphine oxide-containing triarylphosphine oxide derivatives which can be utilized in preparing polyimides having excellent adhesion, fire retardancy and low dielectric constant as well as superior thermal stability and mechanical properties, and preparing method thereof.

6 Claims, 4 Drawing Sheets

TRIARYLPHOSPHINE OXIDE DERIVATIVES CONTAINING FLUORINE SUBSTITUENT AND PREPARING METHOD THEREOF

BACKGROUND OF THE INVENTION

Field of the Invention

The present invention relates to fluorine-containing triarylphosphine oxide derivatives and preparing method thereof. Particularly, the present invention relates to both fluorine- and phosphine oxide-containing triarylphosphine oxide derivatives which can be utilized in preparing polyimides having excellent adhesion, fire retardancy and low dielectric constant as well as superior thermal stability and mechanical properties, and preparing method thereof.

Since a fluorine atom has high electron-negativity, small Van der Waals radius, similar to that of hydrogen atom, and high bonding energy with other atoms, fluorine containing molecules have low surface tension and thus low intermolecular force, high volatility, and low friction coefficient. Especially, fluorine compounds are known to improve processability, insulating capability, and weather resistance since they have the fluorine atom at the outer shell of the compounds.

Fluorine-containing dianhydrides and diamines are widely used to prepare polyimides having excellent processability and low dielectric constant. A demand of these polyimides is constantly increased in energy relating fields such as nuclear power or solar cell, optical communications, applications using optical materials and semiconductor fields.

Recently, polyimides and polyamides having phosphine oxides have been reported to show improved adhesive and fire retardancy. Bis(3-aminophenyl)phenylphosphine oxide (hereinafter referred to as "DAPPO") disclosed by J. E. McGrath et al. at Virginia Tech is one of the examples (M. F. Martinez-Nuez et al., Polymer Preprint, 35, p. 709 (1994)).

Another example is bis(3-aminophenyl-3,5-bistrifluoromethylphenyl)phosphine oxide (hereinafter referred to as "DA6FPPO") having a phosphine oxide and 6 fluorines (K. U. Jeong, J. J. Kim and T. H. Yoon, Korea Polymer Journal, 8, 215–223 (2000) and K. U. Jeong, T. H. Yoon, Korean Patent Application No.1999-50831).

Said DA6FPPO has good processability and low dielectric constant, but relatively low glass transition temperature and poor adhesion due to high concentration of fluorine. As a result, there has been a great demand for new monomers which can be used to prepare polyimides having low dielectric constant without lowering Tg, thermal stability and mechanical properties as well as adhesion.

SUMMARY OF THE INVENTION

To be free of aforementioned problems, the inventors have extensively studied and prepared bis(3-aminophenyl)[4-(trifluoromethyl)phenyl]phosphine oxide monomer (hereinafter referred to as "DA3FPPO"), containing both fluorines and phosphine oxide, which contains less fluorines than DA6FPPO for higher adhesion and Tg without sacrificing excellent mechanical and thermal properties of the conventional polyimides. Therefore, an objective of the present invention is to provide triarylphosphine oxide derivatives having both fluorine(s) and phosphine oxide(s) in order to show superior adhesion and low dielectric constant without sacrificing excellent properties of polyimides.

BRIEF DESCRIPTION OF THE INVENTION

DETAILED DESCRIPTION OF THE INVENTION

Figure 1:
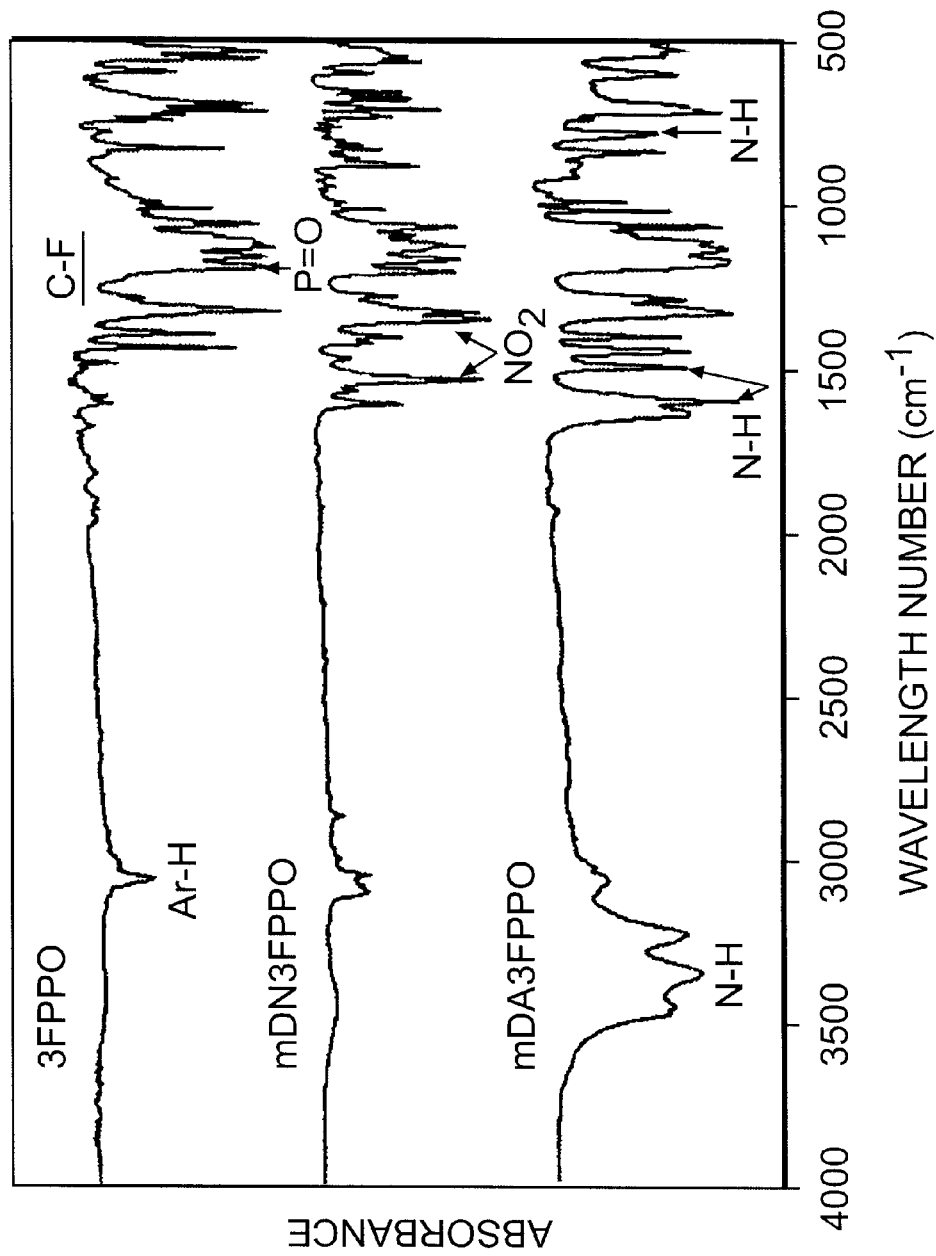
FIG. 1 is FT-IR spectra for the compounds synthesized from Examples 1–3.

The present invention is characterized by fluorine-containing triarylphosphine oxide derivatives expressed by the following formula (1),

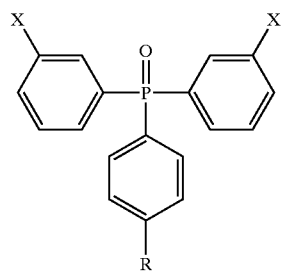

(1)

wherein R is an alkyl independently substituted with fluorine; and X is selected from the group consisting of a hydrogen atom, nitro and amine groups.

The present invention is also characterized by a method of preparing fluorine-containing triarylphosphine oxide derivatives comprising the steps:

1) preparing [4-fluoroalkylphenyl]diphenylphosphine-oxide, expressed by the following formula (1a), by Grignard reaction of bromobenzene substituted with fluoroalkyl group and diphenylphosphinic chloride in an organic solvent and magnesium,

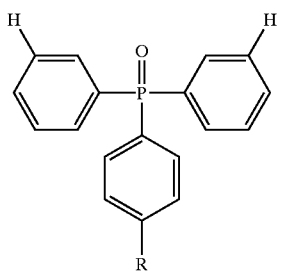

(1a)

wherein R is an alkyl independently substituted with fluorine;

2) preparing bis(3-nitrophenyl)[4-fluoroalkylphenyl]phosphine oxide, expressed by the following formula (1b), by nitration of the compound 1a in sulfuric acid and nitric acid,

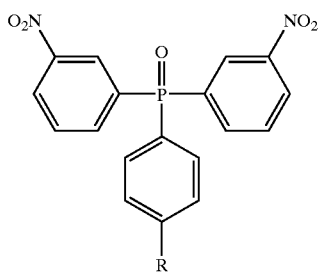

(1b)

wherein R is an alkyl independently substituted with fluorine; and 3) preparing bis(3-aminophenyl)[4-fluoroalkylphenyl] phosphine oxide, expressed by the following formula (1c), by a catalytic hydrogenation of the compound 1b in the presence of palladium,

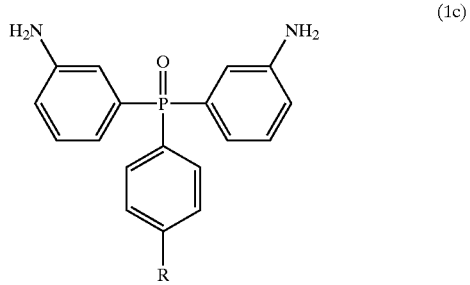

(1c)

wherein R is an alkyl independently substituted with fluorine.

The present invention is described in detail as set forth hereunder.

The compounds of the present invention are prepared by the following Scheme 1, phinic chloride) and the reaction was performed at 0–5° C. for 3 hrs and then at room temperature for 24 hrs.

Nitration was performed by reacting the compound 1a with sulfuric acid and nitric acid at −10 to −5° C. for 3 hrs and then at room temperature for 8 hrs to yield the corresponding compound 1b (X=NO$_2$). The obtained compound 1b was hydrogenated in the presence of palladium in absolute ethanol to yield the corresponding compound 1c (X=NH$_2$).

The triarylphosphine oxide derivatives of the present invention can be polymerized to polyimides, polyamides or co-polymers thereof.

Hereunder is given the more detailed description of the present invention using examples. However, it should not be construed as limiting the scope of the present invention.

EXAMPLE 1

Preparation of [4-(trifluoromethyl)phenyl]diphenylphosphine oxide (Compound 1a; Hereinafter Referred to as "3FPPO")

To a dried 500 mL 3-neck round-bottom flask, equipped with magnetic stirrer, dropping funnel, condenser and nitro- Scheme 1

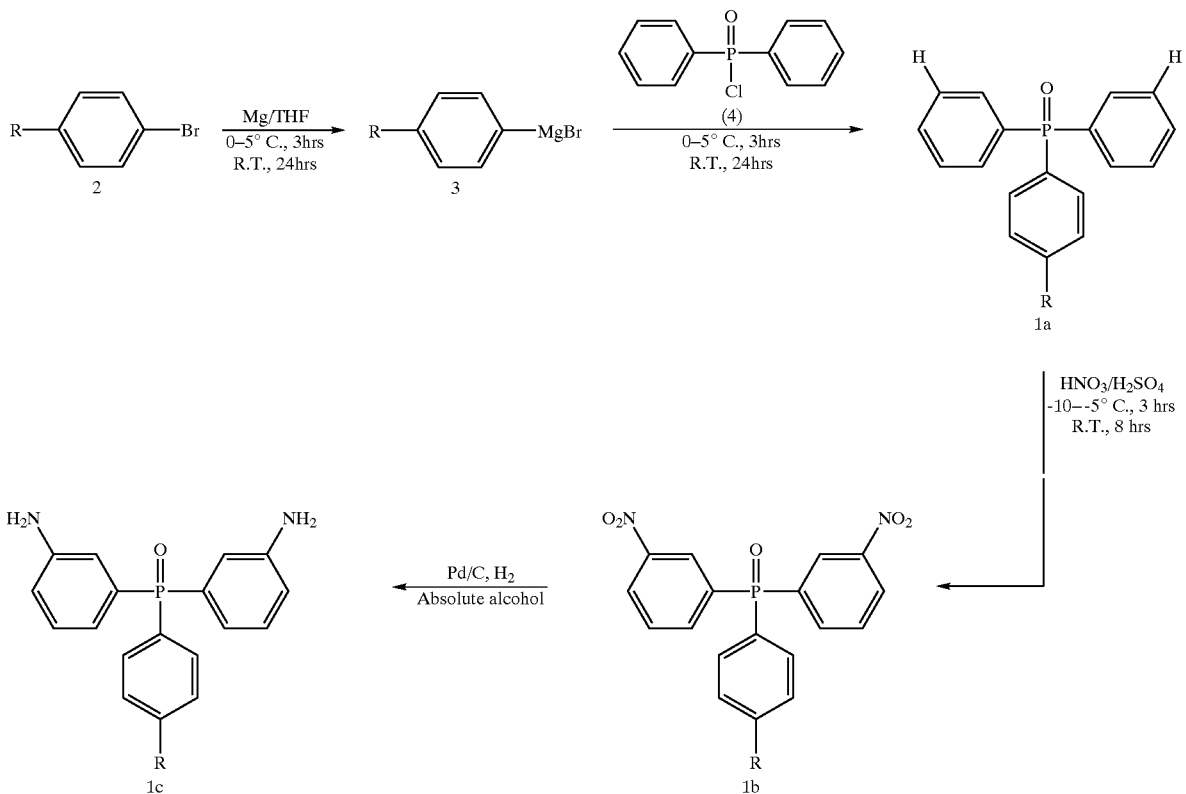

wherein R is an alkyl independently substituted with fluorine.

As shown in Scheme 1, Grignard reagent of formula 3 was prepared by reacting bromobenzene having fluoroalkyl group of formula 2 with magnesium turning in tetrahydrofuran. This Grignard reagent was reacted with diphenylphosphinic chloride of formula 4, called Grignard reaction, to obtain the compound 1a (X=H). A molar ratio of reactants was 1:1 to 1:1.2 (Grignard reagent: diphenylphosgen inlet, were added 1.54 g of magnesium turning (Aldrich) and 60 mL of tetrahydrofuran (Fisher). The reaction mixture was cooled to 0–5° C. in an ice-bath. 11.4 g of 4-(trifluoromethyl)bromobenzene (Aldrich) was added slowly over a period of 3 hrs using a dropping funnel, while maintaining the temperature of 5° C. Then, the reaction solution was allowed to reach room temperature and further reacted for 16 hrs to yield 4-(trifluoromethyl)

phenylmagnesium bromide as a Grignard reagent which was a dark brown solution.

To the reaction mixture cooled to 5° C. in an ice-bath, was slowly added 10 g of diphenyl phosphinic chloride (Aldrich) over a period of 3 hrs using a dropping funnel. Then the reaction solution was allowed to reach room temperature, and reacted further for 24 hrs to give a dark brown solution.

The reaction mixture was washed with 10 mL of 10% sulfuric acid and 2 L of distilled water, and then neutralized with sodium carbonate, followed by extraction with chloroform and water. Then, the organic layer was evaporated to afford 11.7 g(80%) of the desired product (3FPPO) which was further purified by recrystallization with 1 L of hexane.

Figure 2:
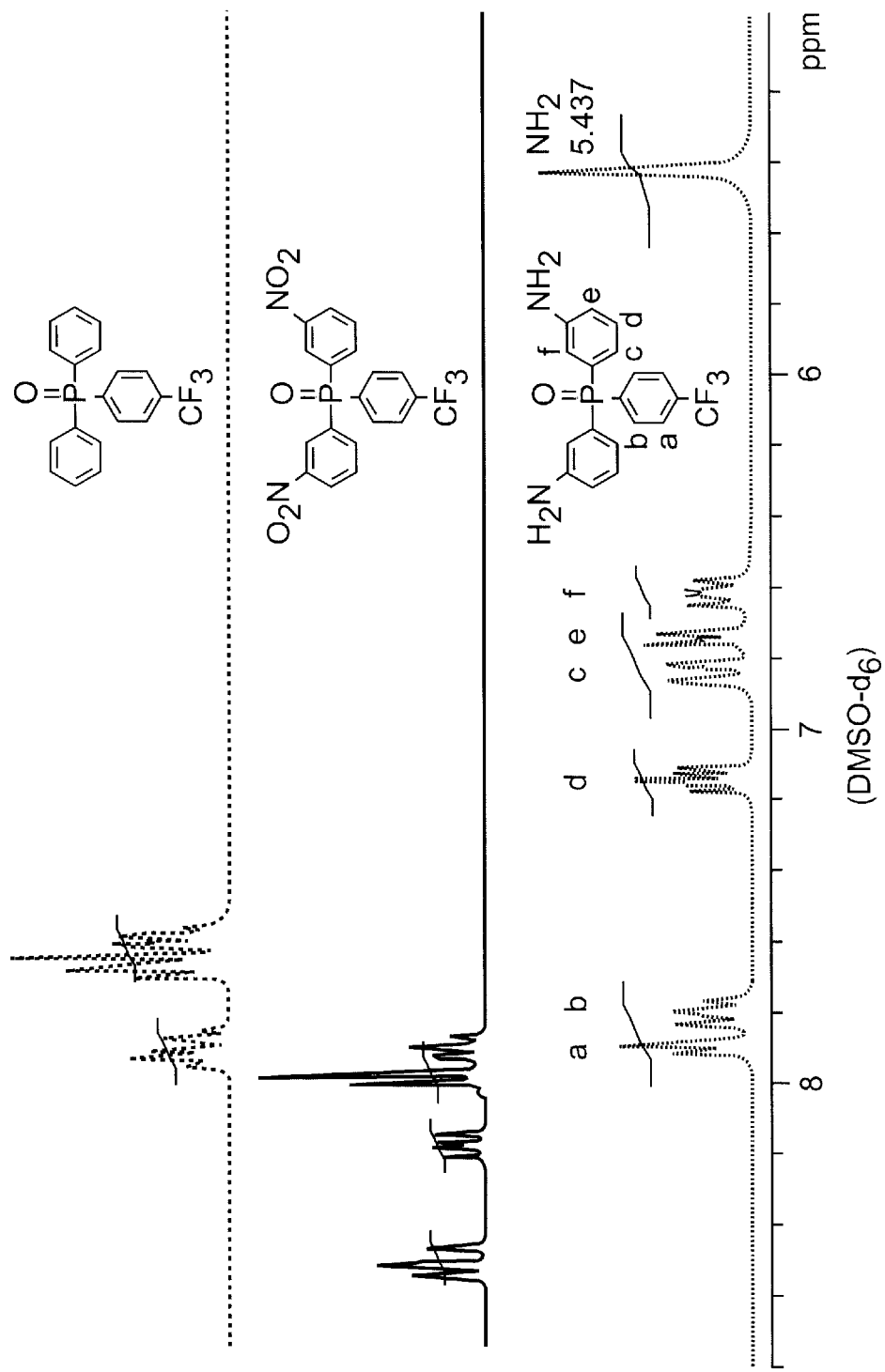
FIG. 2 is $^1$H-NMR spectra for the compounds synthesized from Examples 1–3.
Figure 3:
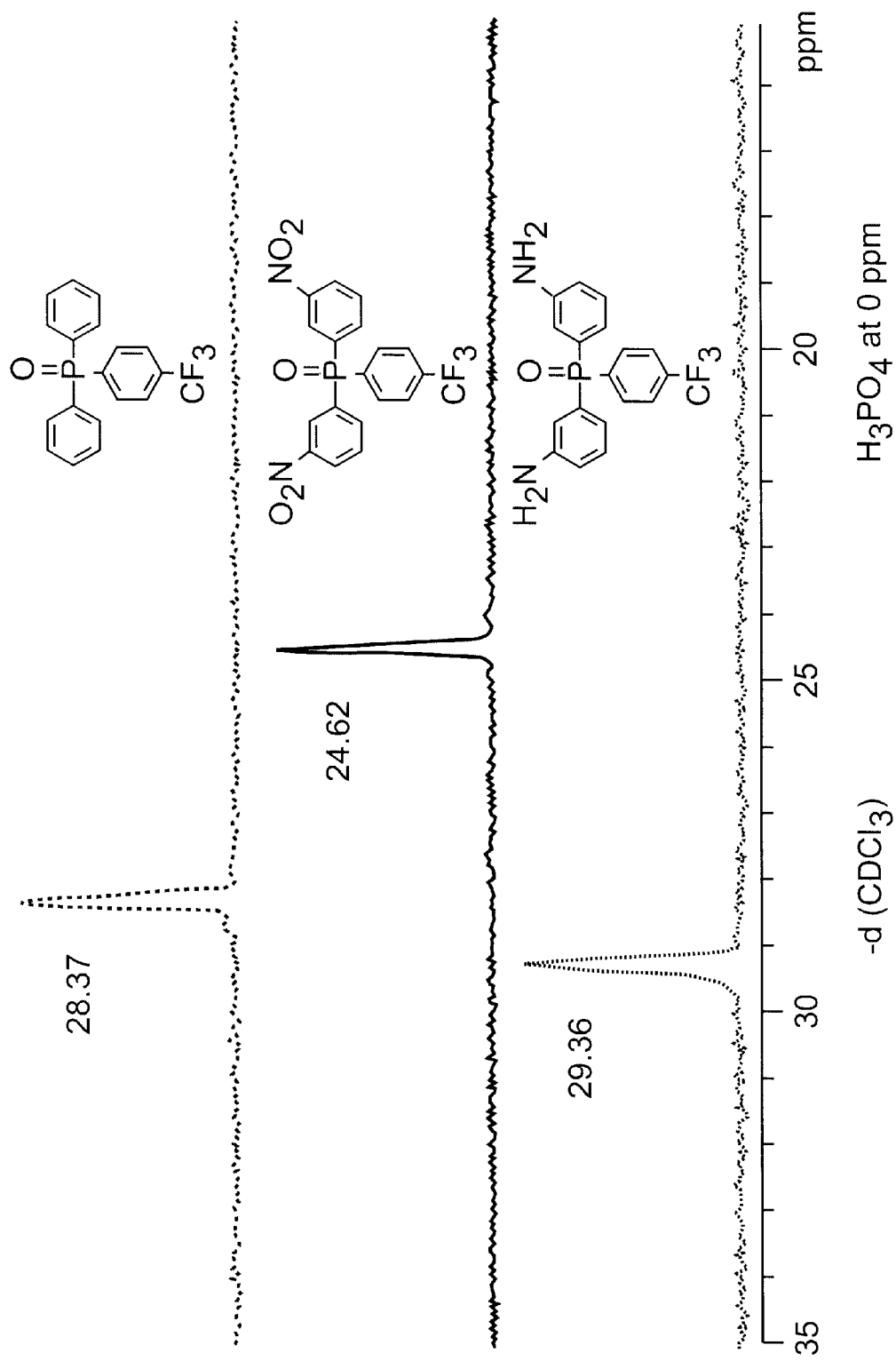
FIG. 3 is $^{31}$P-NMR spectra for the compounds synthesized from Examples 1–3.
Figure 4:
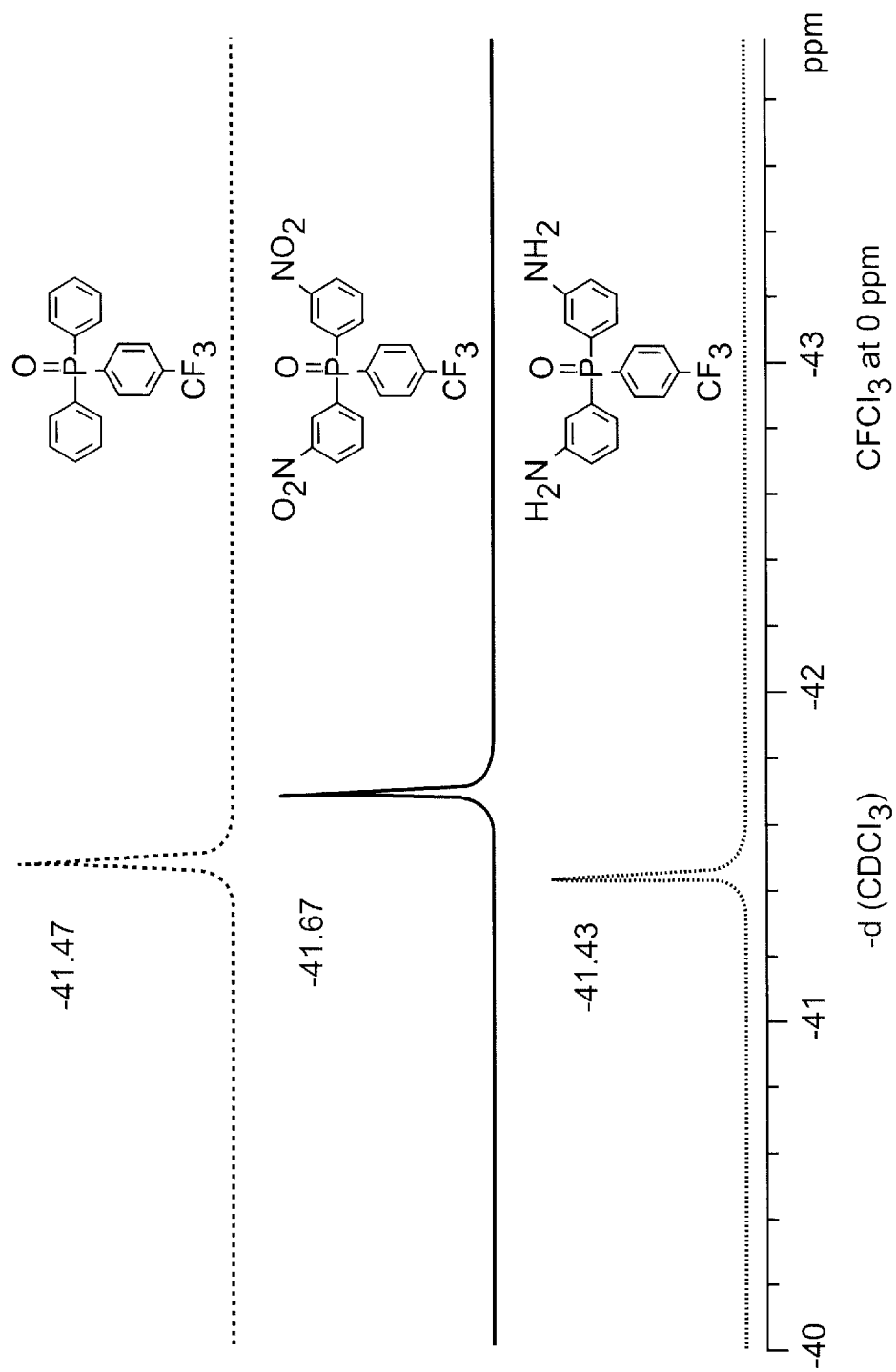
FIG. 4 is $^{19}$F-NMR spectra for the compounds synthesized from Examples 1–3.

The obtained product (3FPPO) was dried in a vacuum oven at 60° C. for 6 hrs and then characterized by FT-IR, $^1$H-NMR, $^{31}$P-NMR, $^{19}$F-NMR and melting point measurement. The melting point was 90.5–91.2° C. and the FT-IR analysis provided C—F bond peaks at 1363–1500 cm$^{-1}$; and P=O stretching peaks at 1190 cm$^{-1}$ as shown in FIG. 1. The $^1$H-NMR analysis (DMSO-d$_6$) showed proton peaks of phenyl ring substituted with fluorines at 7.95–7.84 ppm and proton peaks of diphenyl ring at 7.70–7.56 ppm as shown in FIG. 2. $^{31}$P-NMR and $^{19}$F-NMR (CDCl$_3$) analysis clearly demonstrated successful preparation of the target product showing each singlet at 28.37 and 41.47 ppm as shown in FIGS. 3 and 4.

EXAMPLE 2

Preparation of bis(3-nitrophenyl)-[4-(trifluoromethyl)phenyl]diphenylphosphine oxide (Compound 1b; Hereinafter Referred to as "mDN3FPPO")

3FPPO obtained in Example 1 was nitrated with sulfuric acid and nitric acid to produce the corresponding product mDN3FPPO.

To a dried 250 mL 3-neck round-bottom flask, equipped with magnetic stirrer, dropping funnel, and nitrogen inlet, were added and melted 11.7 g of 3FPPO and 100 mL of sulfuric acid at room temperature. After the reaction mixture was cooled to −10 to −5° C. in a salt-ice bath, 5.14 mL of nitric acid and 15 mL of sulfuric acid were slowly added thereto over a period of 3 hrs. The reaction mixture was further reacted at room temperature for 8 hrs. When the reaction was completed, 1 kg of ice was added to the reaction mixture and extracted with chloroform and water, followed by recrystallization with 1 L of alcohol to produce 13.25 g of mDN3FPPO (90%).

The obtained product (mDN3FPPO) was dried in the vacuum oven at 100° C. for 6 hrs and then characterized by FT-IR, $^1$H-NMR, $^{31}$P-NMR, $^{19}$F-NMR and melting point measurement. The melting point was 202.3–202.9° C. and the FT-IR analysis provided asymmetric stretching peak at 1530 cm$^{-1}$ and symmetric stretching peak at 1350 cm$^{-1}$ for the aromatic nitro compound which was not shown in that of 3FPPO as in FIG. 1. The $^1$H-NMR analysis (DMSO-d$_6$) showed 3 group of peaks at 8.55–8.46 ppm, 8.22–8.04 ppm, and 8.01–7.88 ppm due to the formation of NO$_2$ group as shown in FIG. 2. $^{31}$P-NMR (CDC$_3$) analysis clearly demonstrated the successful formation of NO$_2$ groups showing chemical shift from 28.37 to 24.62 ppm and the sharp single peak elucidated high purity as shown in FIG. 3. $^{19}$F-NMR (CDCl$_3$) analysis was similar to that of 3FPPO because fluorine peak was not affected by the formation of the nitro group.

EXAMPLE 3

Preparation of Bis(3-aminophenyl)-[4-(trifluoromethyl)phenyl]phosphine oxide (Compound 1c; Hereinafter Referred to as "mDA3FPPO")

mDN3FPPO obtained in Example 2 was reduced by the hydrogenation in absolute alcohol in the presence of palladium catalyst (Pd/C) to yield the corresponding product (mDA3FPPO).

To a pressure reactor for the hydrogenation were placed 13.25 g of mDN3FPPO, 200 mL of absolute alcohol and 10–15 mg (2 spoon) of 10% Pd/C. The reaction mixture was reacted at 50° C. under 200 rpm and 100 psi for 24 hrs. The palladium catalyst was removed by filtering through celite and the filtrate was evaporated to obtain solid. The residue was dissolved in water and alcohol (1:9) and recrystallized, followed bysublimation to yield 10.51 g of mDA3FPPO (92%).

The obtained product (mDA3FPPO) was characterized by FT-IR, $^1$H-NMR, $^{31}$P-NMR, $^{19}$F-NMR and melting point measurement. The melting point was 145.0–145.7° C. and the FT-IR analysis provided primary amine stretching peaks at 3450 cm$^{-1}$ and 3340 cm$^{-1}$ and primary amine bending peaks at 1584 cm$^{-1}$ and 1487 cm$^{-1}$ as shown in FIG. 1. The $^1$H-NMR analysis (DMSO-d$_6$) showed proton peaks of phenyl ring substituted with fluorines at 7.90 and 7.80 ppm, 4 proton peaks of phenyl ring substituted with amine at 7.15, 6.85, 6.75, and 6.63 ppm, and a singlet of amine at 5.437 ppm as shown in FIG. 2. $^{31}$P-NMR (CDCl$_3$) analysis clearly demonstrated the successful formation of NH$_2$ group showing chemical shift back from 24.62 to 29.36 ppm as shown in FIG. 3. $^{19}$F-NMR (CDCl$_3$) analysis was similar to that of 3FPPO because fluorine peak was not affected by the formation of the amine group.

Accordingly, the fluorine-containing triarylphosphine oxide derivatives of the present invention are useful in the preparation of polyimide polymers having superior adhesion, fire retardancy and low dielectric constant as well as inherent characteristics of polyimides such as excellent thermal stability and mechanical properties. And further, such prepared polymers according to the present invention are suitable for semiconductor package materials, intermediates for optical fibers and optical materials, and adhesives for metals.

What is claimed is:

1. Fluorine-containing triarylphosphine oxide derivatives expressed by the following formula 1,

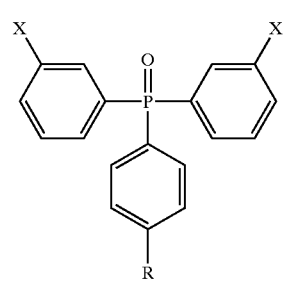

(1)

wherein R is an alkyl independently substituted with fluorine; and X is selected from the group consisting of nitro and amine groups.

2. A method of preparing fluorine-containing triarylphosphine oxide derivatives, expressed by the following formula (1c), comprising the steps:

1) preparing [4-fluoroalkylphenyl]diphenylphosphine oxide, expressed by the following formula (1a), by Grignard reaction of bromobenzene substituted with fluoroalkyl group and diphenylphosphinic chloride in an organic solvent and magnesium,

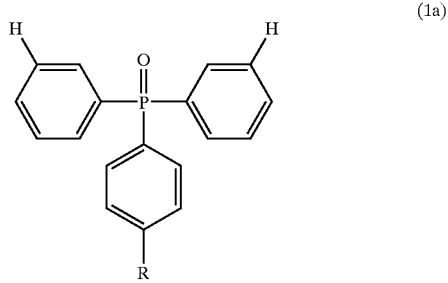
(1a)

wherein R is an alkyl independently substituted with fluorine;

2) preparing bis(3-nitrophenyl)[4-fluoroakylphenyl] phosphine oxide, expressed by the following formula (1b), by nitration of the compound (1a) in sulfuric acid and nitric acid,

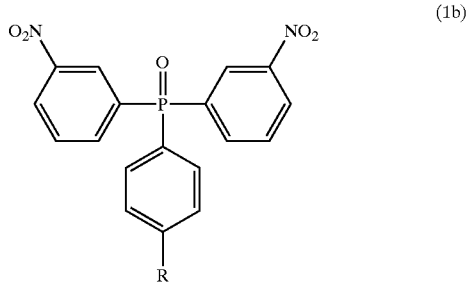
(1b)

wherein R is an alkyl independently substituted with fluorine; and 3) preparing bis(3-aminophenyl)[4-fluoroakylphenyl] phosphine oxide, expressed by the following formula (1c), by a catalytic hydrogenation of the compound 1b in the presence of palladium,

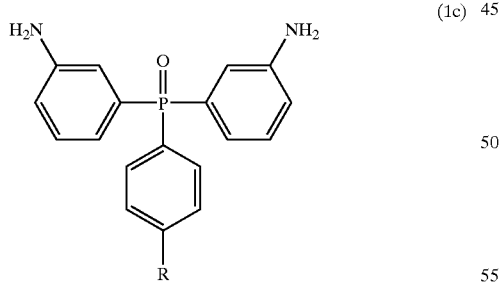
(1c)

wherein R is an alkyl independently substituted with fluorine.

3. The method of preparing fluorine-containing triarylphosphine oxide derivatives according to claim 2, wherein a molar ratio of reactants in said Grignard reaction ranges from 1:1 to 1:1.2.

4. The method of preparing fluorine-containing triarylphosphine oxide derivatives according to claim 2, wherein said hydrogenation is carried out in absolute ethanol as a solvent to produce the compound (1c).

5. A method of preparing fluorine-containing triarylphosphine oxide derivatives, expressed by the following formula (1b), comprising the steps:

1) preparing [4-fluoroalkylphenyl]diphenylphosphine oxide, expressed by the following formula (1a), by Grignard reaction of bromobenzene substituted with fluoroalkyl group and diphenylphosphinic chloride in an organic solvent and magnesium,

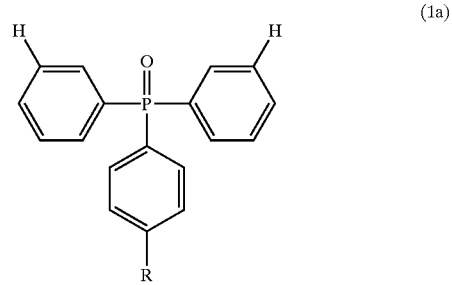
(1a)

wherein R is an alkyl independently substituted with fluorine; and 2) preparing bis(3-nitrophenyl)[4-fluoroakylphenyl] phosphine oxide, expressed by the following formula (1b), by nitration of the compound 1a in sulfuric acid and nitric acid,

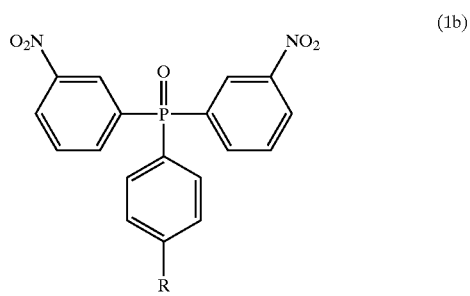
(1b)

wherein R is an alkyl independently substituted with fluorine.

6. The method of preparing fluorine-containing triarylphosphine oxide derivatives according to claim 5, wherein a molar ratio of reactants in said Grignard reaction ranges from 1:1 to 1:1.2.

* * * * *

UNITED STATES PATENT AND TRADEMARK OFFICE
CERTIFICATE OF CORRECTION

PATENT NO.    : 6,531,633 B2                                                Page 1 of 1
DATED         : March 11, 2003
INVENTOR(S)   : Tae-Ho Yoon et al.

It is certified that error appears in the above-identified patent and that said Letters Patent is hereby corrected as shown below:

<u>Column 7,</u>
Lines 21-22, "bis(3-nitrophenyl)[4-fluoroakylphenyl]phosphine" should read
-- bis(3-nitrophenyl)[4-fluoroalkylphenyl]phosphine --.
Lines 40-41, "bis(3-aminophenyl)[4-fluoroakylphenyl]phosphine" should read
-- bis(3-aminophenyl)[4-fluoroalkylphenyl]phosphine --.

<u>Column 8,</u>
Lines 34-35, "bis(3-nitrophenyl)[4-fluoroakylphenyl]phosphine" should read
-- bis(3-nitrophenyl)[4-fluoroalkylphenyl]phosphine --.

Signed and Sealed this

Twenty-second Day of April, 2003

JAMES E. ROGAN
*Director of the United States Patent and Trademark Office*